(12) United States Patent
Ceresa et al.

(10) Patent No.: US 11,883,511 B2
(45) Date of Patent: Jan. 30, 2024

(54) THICKENING SILICA AS FLUORIDE CARRIER FOR TAILORED DELIVERY AND SLOW RELEASE

(71) Applicant: GABA International Holding GmbH, Therwil (CH)

(72) Inventors: Alan Ceresa, Therwil (CH); Michael Neumann, Therwil (CH); Madeleine Manns, Laufen (CH); Nathalie Coq-Bernard, Muespach le Haut (FR); Andre Brunella, Dornach (CH); Marian Holerca, Somerset, NJ (US); Thomas Schollbach, Basel (CH)

(73) Assignee: GABA International Holding GmbH, Therwil (CH)

( * ) Notice: Subject to any disclaimer, the term of this patent is extended or adjusted under 35 U.S.C. 154(b) by 57 days.

(21) Appl. No.: 17/247,199

(22) Filed: Dec. 3, 2020

(65) Prior Publication Data

US 2021/0177712 A1    Jun. 17, 2021

Related U.S. Application Data

(60) Provisional application No. 62/947,265, filed on Dec. 12, 2019.

(51) Int. Cl.
| | |
|---|---|
| *A61K 8/25* | (2006.01) |
| *A61K 8/21* | (2006.01) |
| *A61Q 11/00* | (2006.01) |
| *A61K 8/02* | (2006.01) |

(52) U.S. Cl.
CPC ............ *A61K 8/02* (2013.01); *A61K 8/25* (2013.01); *A61Q 11/00* (2013.01); *A61K 2800/48* (2013.01)

(58) Field of Classification Search
CPC ...... A61K 8/25; A61K 8/21; A61K 2800/412; A61K 2800/48; A61K 2800/60; A61K 8/02; A61Q 11/00; A61Q 17/005
See application file for complete search history.

(56) References Cited

U.S. PATENT DOCUMENTS

| | | | |
|---|---|---|---|
| 4,172,121 A | 10/1979 | Calvin et al. | |
| 6,214,383 B1 * | 4/2001 | Esch | A61Q 11/00 424/489 |
| 6,375,934 B1 * | 4/2002 | Eklund | A61B 5/14539 424/52 |
| 2011/0236444 A1 * | 9/2011 | Darsillo | A61K 8/27 424/401 |
| 2016/0213023 A1 * | 7/2016 | Ortiz De Zarate | A23G 4/10 |
| 2019/0183748 A1 | 6/2019 | Bhadra et al. | |

FOREIGN PATENT DOCUMENTS

| | | |
|---|---|---|
| CN | 101340885 | 1/2009 |
| FR | 2883278 | 9/2006 |
| WO | 2002/02060 | 1/2002 |
| WO | 2007/076396 | 7/2007 |
| WO | 2019/120467 | 6/2019 |

OTHER PUBLICATIONS

Andrea Gallo Di Luigi S.r.l. Silice Amorfa Tixosil 331. Jan. 28, 2014. <http://www.andreagallo.it/images/schedepdf/TDS/SILICE_AMORFA_TIXOSIL_331_820245_tds.pdf>. (Year: 2014).*

* cited by examiner

*Primary Examiner* — Tracy Liu

(57) ABSTRACT

Disclosed are oral care compositions comprising a thickening silica and a fluoride ion source, wherein fluoride is absorbed on the thickening silica and wherein the pH of the composition is below 5.5, as well as to methods of using these compositions. The thickening silica may have a particle size distribution (D95) less than or equal to 7 μm and a BET surface area of greater than or equal to 150 m$^2$/g.

16 Claims, 2 Drawing Sheets

THICKENING SILICA AS FLUORIDE CARRIER FOR TAILORED DELIVERY AND SLOW RELEASE

CROSS REFERENCE TO RELATED APPLICATIONS

This application claims the benefit and priority of U.S. provisional application 62/947,265, filed on Dec. 12, 2019.

BACKGROUND

Fluoride is one of the agents commonly used to combat dental caries. Fluoride can greatly help dental health by strengthening the tooth enamel, making it more resistant to tooth decay. Fluoride also helps remineralize weakened tooth enamel and reverses early signs of tooth decay. Many oral care products such as toothpastes, mouthwashes and professional dental treatment products contain fluoride. In order to be effective, fluoride has to be delivered to the enamel surface effectively. The choice of formulation ingredients is important in determining whether or not fluoride is effectively delivered to the enamel surface. There remains a need in the art for oral care compositions with improved delivery of fluoride to the enamel surface.

BRIEF SUMMARY

In one aspect, the invention provides an oral care composition comprising an orally acceptable vehicle, a thickening silica and a fluoride ion source, wherein fluoride (fluoride ion) is absorbed on the thickening silica, wherein the thickening silica has a particle size distribution (D95) less than or equal to 7 μm and a BET surface area of greater than or equal to 150 $m^2/g$, and wherein the pH of the composition is below 5.5. In some embodiments, the thickening silica may have a BET surface area of greater than or equal to 175 $m^2/g$, greater than or equal to 200 $m^2/g$, or greater than or equal to 250 $m^2/g$. In some embodiments, the thickening silica may have an oil absorption of greater than or equal to about 200 mL/100 g, about 240 mL/100 g, or about 250 mL/100 g. In some embodiments, the thickening silica may have an average particle size of from about 3 μm to about 5 μm, from about 3 μm to about 4 μm, or about 3.5 μm. In a preferred embodiment, the thickening silica is Tixosil 331.

In some embodiments, the thickening silica may be present in an amount of from about 1 weigh % to about 20 weight %, from about 1 weight % to about 10 weight %, from about 2 weight % to about 10 weight %, about 4 weight % to about 6 weight %, about 4.5 weight % to about 5.5 weight %, about 4.8 weight % to about 5.2 weight %, or about 5.0 weight %, based on a total weight of the oral care composition.

In some embodiments, the fluoride ion source may be selected from sodium fluoride, stannous fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination thereof. In a preferred embodiment, the fluoride ion source is sodium fluoride.

In some embodiments, the fluoride ion source may be present in amounts sufficient to supply 25 ppm to 5,000 ppm of fluoride ions, generally at least 500 ppm, e.g., 500 to 2000 ppm, e.g., 1000 ppm to 1600 ppm, e.g., 1450 ppm.

In some embodiments, the amount of fluoride absorbed on the thickening silica is from 1% to 20% by weight of the thickening silica. In some embodiments, the amount of fluoride absorbed on the thickening silica is from 2% to 20%, e.g., from 5% to 20%, from 10% to 20%, from 15% to 20%, from 16% to 20%, from 17% to 20%, from 18% to 20%, or from 18% to 19%, by weight of the thickening silica.

In another aspect, the invention provides a method comprising applying an effective amount of any of oral care compositions as disclosed herein to the oral cavity, e.g., by brushing, to a subject in need thereof, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

In another aspect, the invention provides a method of preparing a thickening silica loaded with fluoride, which comprises mixing a thickening silica and a fluoride ion source in an aqueous solution (e.g., water) at a pH below 5.5, e.g., from 3.5 to 5.5, from 3.5 to 5.0, from 3.5 to 4.5, from 4.0 to 5.0, from 4.0 to 4.5, from 3.5 to 4.0, from 3.8 to 4.2, or about 4.0, wherein the thickening silica has a particle size distribution (D95) less than or equal to 7 μm and a BET surface area of greater than or equal to 150 $m^2/g$. In some embodiments, the thickening silica may have a BET surface area of greater than or equal to 175 $m^2/g$, greater than or equal to 200 $m^2/g$, or greater than or equal to 250 $m^2/g$. In some embodiments, the thickening silica may have an oil absorption of greater than or equal to about 200 mL/100 g, about 240 mL/100 g, or about 250 mL/100 g. In some embodiments, the thickening silica may have an average particle size of from about 3 μm to about 5 μm, from about 3 μm to about 4 μm, or about 3.5 μm. In a preferred embodiment, the thickening silica is Tixosil 331.

In another aspect, the invention provides an oral care composition comprising a thickening silica loaded with fluoride prepared by any of methods as disclosed herein. The fluoride absorbed on the thickening silica is released at pH of 8.0.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The present invention will become more fully understood from the detailed description and the accompanying drawings.

DETAILED DESCRIPTION

Figure 1:
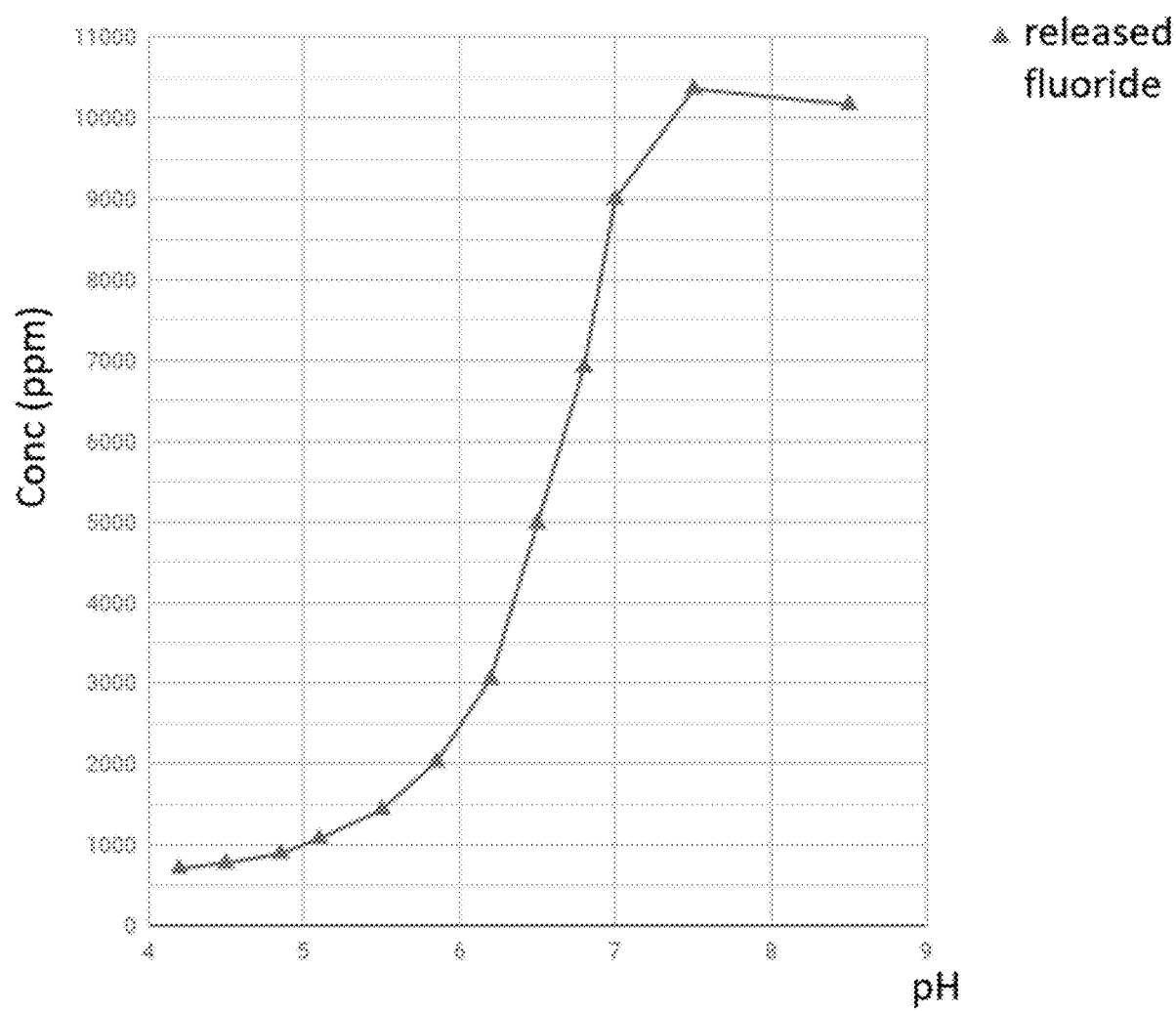
FIG. 1 is a graph showing the release of fluoride from the silica fluoride when pH of the solution is changed.

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention relates to use of a thickening silica which has a particle size distribution (D95) less than or equal to 7 μm and a BET surface area of greater than or equal to 150 m$^2$/g as a fluoride carrier for a tailored delivery of fluoride to the dentin and in-situ slow release of fluoride. It has been found that most of fluoride is bound to the thickening silica (e.g., Tixosil 331) when the thickening silica and fluoride are mixed in an aqueous solution at a low pH (e.g., 4.0). It has been further found that the absorption process can be easily reversed by changing the pH to 8 and that the release of fluoride is a slow process, i.e., by changing the pH of the solution from 4.0 to 8.0, a full release of the fluoride takes approximately 400 s, i.e. 3-4 time more than a normal teeth brushing time. These findings are interesting as most of fluoride will be absorbed on the thickening silica in an oral care composition having a low pH. However, upon use, fluoride will be released in the mouth after equilibration at the physiological pH in the oral cavity, which is approximately 7 to 8. Combined with the fact that Tixosil 331 can adhere to the dentin and occlude dentin tubules and is thus effective in reducing dental sensitivity, as shown in WO 2019/120467, the thickening silica loaded with fluoride can be used to reduces tooth hypersensitivity and at the same time deliver fluoride to the dentin effectively. The slow release of fluoride in the mouth allows the thickening silica to reach and adhere on the dentin before fluoride is released.

The present invention provides, in an aspect, an oral care composition (Compositions 1.0), e.g., toothpaste or gel, comprising an orally acceptable vehicle, a thickening silica and a fluoride ion source, wherein the thickening silica has a particle size distribution (D95) less than or equal to 7 μm and a BET surface area of greater than or equal to 150 m$^2$/g, and wherein the pH of the composition is below 5.5.

For example, the invention includes:
1.1. Composition 1.0, wherein fluoride (fluoride ion) is absorbed on the thickening silica.
1.2. Any of the preceding compositions, wherein the thickening silica has a BET surface area of greater than or equal to 175 m$^2$/g, greater than or equal to 200 m$^2$/g, or greater than or equal to 250 m$^2$/g.
1.3. Any of the preceding compositions, wherein the thickening silica has an average particle size of from about 3 μm to about 5 μm, from about 3 μm to about 4 μm, or about 3.5 μm.
1.4. Any of the preceding compositions, wherein the thickening silica has an oil absorption of greater than or equal to about 200 mL/100 g, about 240 mL/100 g, or about 250 mL/100 g.
1.5. Any of the preceding compositions, wherein the thickening silica is Tixosil 331.
1.6. Any of the preceding compositions, wherein the thickening silica is present in an amount of from about 1 weight % to about 20 weight %, from about 1 weight % to about 10 weight %, from about 2 weight % to about 10 weight %, about 4 weight % to about 6 weight %, about 4.5 weight % to about 5.5 weight %, about 4.8 weight % to about 5.2 weight %, or about 5.0 weight %, based on a total weight of the oral care composition.
1.7. Any of the preceding compositions, wherein the fluoride ion source is selected from sodium fluoride, stannous fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination thereof.
1.8. Any of the preceding compositions, wherein the fluoride ion source is sodium fluoride.
1.9. Any of the preceding compositions, wherein the fluoride ion source is present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.
1.10. Any of the preceding compositions, wherein the amount of fluoride absorbed on the thickening silica is from 1% to 20%, e.g., from 2% to 20%, from 5% to 20%, from 10% to 20%, from 15% to 20%, from 16% to 20%, from 17% to 20%, from 18% to 20%, or from 18% to 19%, by weight of the thickening silica.
1.11. Any of the preceding compositions, wherein the pH of the composition is from 3.5 to 5.5, from 3.5 to 5.0, from 3.5 to 4.5, from 4.0 to 5.5, from 4.5 to 5.5, from 4.0 to 5.0, from 4.0 to 4.5, from 3.8 to 4.2, from 4.2 to 4.8, from 4.2 to 4.6, about 4.0, about 4.1, about 4.2, about 4.3, about 4.4 or about 4.5.
1.12. Any of the preceding compositions, wherein the fluoride absorbed on the thickening silica is released at pH of 8.0.
1.13. Any of the preceding compositions, wherein the composition further comprises additional thickeners other than the thickening silica.
1.14. Any of the preceding compositions, wherein the composition comprising an abrasive.
1.15. Any of the preceding compositions, wherein the abrasive is selected from silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, and combinations thereof.
1.16. Any of the preceding compositions, wherein the abrasive is selected from calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive, and combinations thereof.
1.17. Any of the preceding compositions, wherein the abrasive is present in an amount of from 10% to 70%, e.g., from 10% to 30%, e.g., 10% to 20%, 15% to 25%, from 20% to 50%, from 25% to 45%, or from 30% to 40% by weight of the composition.
1.18. Any of the preceding compositions, wherein the abrasive comprises a silica abrasive.

1.19. Any of the preceding compositions, wherein the silica abrasive is present in an amount of from 10% to 30%, e.g., 10% to 20%, 15% to 25%, or about 15%, by weight of the composition.
1.20. Any of the preceding compositions wherein the composition comprises a zinc ion source.
1.21. Any of the preceding compositions, wherein the zinc ion source is present an amount of from 0.01% to 5%, e.g., 0.1% to 4%, or 0.5% to 3%, by weight of the composition.
1.22. Any of the preceding compositions, wherein zinc ion source is selected from the group consisting of zinc oxide, zinc sulfate, zinc chloride, zinc citrate, zinc lactate, zinc gluconate, zinc malate, zinc tartrate, zinc carbonate, zinc phosphate and a combination thereof.
1.23. Any of the preceding compositions, wherein the zinc ion source is selected from zinc citrate, zinc oxide and a combination thereof.
1.24. Any of the preceding compositions, wherein zinc oxide is present in an amount of 0.5% to 2%, e.g., 0.5% to 1.5%, or about 1% by weight of the composition.
1.25. Any of the preceding compositions, wherein zinc citrate is present in an amount of 0.1% to 1%, 0.25 to 0.75%, or about 0.5% by weight of the composition.
1.26. Any of the preceding compositions, wherein the composition comprises a basic amino acid.
1.27. Any of the preceding compositions, wherein the basic amino acid comprises one or more of arginine, lysine, citrulline, ornithine, creatine, histidine, diaminobutanoic acid, diaminoproprionic acid, salts thereof, or combinations thereof.
1.28. Any of the preceding compositions, wherein the basic amino acid has the L-configuration.
1.29. Any of the preceding compositions, wherein the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.
1.30. Any of the preceding compositions, wherein the basic amino acid comprises arginine.
1.31. Any of the preceding compositions, wherein the basic amino acid comprises L-arginine.
1.32. Any of the preceding compositions, wherein the basic amino acid comprises arginine bicarbonate, arginine phosphate, arginine sulfate, arginine hydrochloride or combinations thereof, optionally wherein the basic amino acid is arginine bicarbonate.
1.33. Any of the preceding compositions wherein the composition comprises a surfactant, e.g., selected from anionic, cationic, zwitterionic, nonionic surfactants, and mixtures thereof, e.g., in an amount of from 0.01% to 5%, from 0.01% to 2%, from 1% to 2%, or about 1.5%, by weight of the composition.
1.34. Any of the preceding compositions, wherein the composition comprises a humectant.
1.35. Composition 1.34, wherein the humectant comprises glycerin or sorbitol, optionally wherein glycerin or sorbitol is present in an amount of from 15% to 40%, from 20% to 40%, from 30% to 40%, or about 35% by weight of the composition.
1.36. Any of the preceding compositions, wherein the composition comprises one or more soluble phosphate salts, e.g. selected from tetrasodium pyrophosphate (TSPP), sodium tripolyphosphate (STPP) and a combination thereof.
1.37. Any foregoing composition, wherein the composition comprises flavoring, fragrance and/or coloring.
1.38. Any foregoing composition, wherein the composition comprises an effective amount of one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
1.39. Any foregoing composition, wherein the composition comprises a whitening agent, e.g., selected from the group consisting of peroxides, metal chlorites, perborates, percarbonates, peroxyacids, hypochlorites, and combinations thereof.
1.40. Any foregoing composition, wherein the composition comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate).
1.41. Any foregoing composition, wherein the composition comprises an agent that interferes with or prevents bacterial attachment, e.g., solbrol or chitosan.
1.42. Any foregoing composition, wherein the composition comprises a soluble calcium salt, e.g., selected from calcium sulfate, calcium chloride, calcium nitrate, calcium acetate, calcium lactate, and combinations thereof
1.43. Any foregoing composition, wherein the composition comprises a physiologically or orally acceptable potassium salt, e.g., potassium nitrate or potassium chloride, in an amount effective to reduce dentinal sensitivity.
1.44. Any foregoing composition, wherein the composition comprises a breath freshener, fragrance or flavoring.
1.45. Any of the preceding compositions, wherein the composition comprises water, optionally wherein water is present in an amount of from 1% to 80%, from 10% to 80%, from 20% to 60%, from 20% to 40%, from 10% to 30%, from 20% to 30%, from 1% to 20%, from 25% to 35%, from 1% to 10%, from 1% to 5%, or from 5% to 10%, by weight of the composition.

1.46. Any of the preceding compositions, wherein the composition is selected from the group consisting of toothpaste, gel, water free toothpaste, tooth powder, or dental varnish.

1.47. Any of the preceding compositions, wherein the composition is a toothpaste, gel or dental varnish.

1.48. Any of the preceding compositions, wherein the composition is a toothpaste.

1.49. Any of the preceding compositions for use in (i) reducing or inhibiting formation of dental caries, (ii) reducing, repairing or inhibiting pre-carious lesions of the enamel, (iii) reducing or inhibiting demineralization and promote remineralization of the teeth, (iv) reducing hypersensitivity of the teeth, (v) reducing or inhibiting gingivitis, (vi) promoting healing of sores or cuts in the oral cavity, (vii) reducing levels of acid producing bacteria, (viii) reducing or inhibiting microbial biofilm formation in the oral cavity, (ix) reducing or inhibiting plaque formation in the oral cavity, (x) promoting systemic health, or (xi) cleaning teeth and oral cavity.

The oral care composition of the invention can be in the form of any oral care formulations, including dentifrice, toothpaste, water free toothpaste, gel, mouthwash, powder, cream, strip, gum, bead, film, floss, dental varnish or any other known in the art. In some embodiments, the oral care composition is a toothpaste or gel. In some embodiments, the oral care composition is a toothpaste.

The oral care composition of the invention may be a single phase oral care composition. For example, all the components of the oral care composition may be maintained together with one another in a single phase and/or vessel. For example, all the components of the oral care composition may be maintained in a single phase, such as a single homogenous phase. In another embodiment, the oral care composition may be a multi-phase oral care composition.

The oral care composition of the invention may contain an orally acceptable vehicle. As used herein, an "orally acceptable vehicle" refers to a material or combination of materials that are safe for use in the compositions of the invention, commensurate with a reasonable benefit/risk ratio. Such materials include but are not limited to, for example, water, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared. In some embodiment, the orally acceptable vehicle may include an orally acceptable solvent. Illustrative solvents may include, but are not limited to, one or more of ethanol, phenoxyethanol, isopropanol, water, cyclohexane, methyl glycol acetate, benzyl alcohol, or the like, or any mixture or combination thereof. In a particular embodiment, the orally acceptable solvent includes benzyl alcohol.

In some embodiments, water may be present in the oral compositions of the invention. Water employed in the preparation of commercial oral compositions should be deionized and free of organic impurities. Water commonly makes up the balance of the compositions and includes from 1% to 80%, from 10% to 80%, from 20% to 60%, from 20% to 40%, from 10% to 30%, from 20% to 30%, from 1% to 20%, from 25% to 35%, from 1% to 10%, from 1% to 5%, or from 5% to 10%, by weight of the oral compositions. This amount of water includes the free water which is added plus that amount which is introduced with other materials such as with sorbitol or any components of the invention. In other embodiments, the composition may be substantially free of water, e.g., the composition may contain water in an amount of less than 1%, less than 0.1%, or less than 0.01%. In some embodiments, the composition does not contain water. In certain embodiments, the composition is a water free toothpaste.

The oral care composition of the invention comprises a thickening silica having a particle size distribution (D95) less than or equal to 7 μm and a BET surface area of greater than or equal to 150 $m^2/g$, and a fluoride ion source. In the composition of the invention wherein the pH of the composition is below 5.5, fluoride is absorbed on the thickening agent. As used herein, the terms "absorbed", and "loaded with" mean that fluoride (fluoride ions) is bound to thickening silicas so that fluoride does not move freely. In some embodiments, the amount of fluoride absorbed on the thickening silica is from 1% to 20%, e.g., from 2% to 20%, from 5% to 20%, from 10% to 20%, from 15% to 20%, from 16% to 20%, from 17% to 20%, from 18% to 20%, or from 18% to 19%, by weight of the thickening silica. The fluoride absorbed on the thickening silica is released at pH of 8.0.

The thickening silica present in the oral care composition of the present invention has a particle size distribution (D95) less than or equal to 7 μm and a BET surface area of greater than or equal to 150 $m^2/g$. In some embodiments, the thickening silica may have a BET surface area of greater than or equal to 175 $m^2/g$, greater than or equal to 200 $m^2/g$, or greater than or equal to 250 $m^2/g$. In some embodiments, the thickening silica may have an oil absorption of greater than or equal to about 200 mL/100 g, about 240 mL/100 g, or about 250 mL/100 g. In some embodiments, the thickening silica may have an average particle size of from about 3 μm to about 5 μm, from about 3 μm to about 4 μm, or about 3.5 μm. In a preferred embodiment, the thickening silica is Tixosil 331, which is commercially available from Solvay of Bruxelles, Belgium.

In some embodiments, the thickening silica may be present in an amount of from about 1 weight % to about 20 weight %, e.g., from about 1 weight % to about 10 weight %, from about 2 weight % to about 10 weight %, about 4 weight % to about 6 weight %, about 4.5 weight % to about 5.5 weight %, about 4.8 weight % to about 5.2 weight %, or about 5.0 weight %, based on a total weight of the oral care composition.

The oral care composition of the invention includes fluoride, such as one or more fluoride ion sources (e.g., soluble fluoride salts). A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In some embodiment, the fluoride ion source includes sodium fluoride. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.

In some embodiments, the pH of the oral care composition of the invention may be from 3.5 to 5.5, from 3.5 to 5.0, from 3.5 to 4.5, from 4.0 to 5.5, from 4.5 to 5.5, from 4.0 to 5.0, from 4.0 to 4.5, from 3.8 to 4.2, from 4.2 to 4.8, from 4.2 to 4.6, about 4.0, about 4.1, about 4.2, about 4.3, about 4.4 or about 4.5.

The oral care composition of the invention may include one or more pH modifying agents. For example, the oral care composition may include one or more acidifying agents and/or one or more basifying agents configured to reduce and/or increase the pH thereof, respectively. Illustrative acidifying agents and/or one or more basifying agents may be or include, but are not limited to, an alkali metal hydroxide, such as sodium hydroxide and/or potassium hydroxide, citric acid, hydrochloric acid, or the like, or combinations thereof.

The oral care composition of the invention may also include one or more buffering agents configured to control or modulate the pH within a predetermined or desired range. Illustrative buffering agents may include, but are not limited to, sodium bicarbonate, sodium phosphate, sodium carbonate, sodium acid pyrophosphate, sodium citrate, and mixtures thereof. Sodium phosphate may include monosodium phosphate ($NaH_2PO_4$), disodium phosphate ($Na_2HPO_4$), trisodium phosphate ($Na_3PO_4$), and mixtures thereof. In a typical embodiment, the buffering agent may be anhydrous sodium phosphate dibasic or disodium phosphate and/or sodium phosphate monobasic. In another embodiment, the buffering agent includes anhydrous sodium phosphate dibasic or disodium phosphate, and phosphoric acid (e.g., syrupy phosphoric acid; 85%-Food Grade).

The oral care composition of the invention may comprise a basic amino acid in free or salt form. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrulline, ornithine, creatine, histidine, diaminobutanoic acid, diaminopropionic acid, salts thereof or combinations thereof. In a particular embodiment, the basic amino acids are selected from arginine, lysine, citrulline, and ornithine. The basic amino acids may generally be present in the L-form or L-configuration. The basic amino acids may be provided as a salt of a di- or tri-peptide including the amino acid. In some embodiments, at least a portion of the basic amino acid present in the oral care composition is in the salt form. In some embodiments, the basic amino acid is arginine, for example, L-arginine, or a salt thereof. Arginine may be provided as free arginine or a salt thereof. For example, arginine may be provided as arginine phosphate, arginine hydrochloride, arginine sulfate, arginine bicarbonate, or the like, and mixtures or combinations thereof. The basic amino acid may be provided as a solution or a solid. For example, the basic amino acid may be provided as an aqueous solution. In some embodiment, the amino acid includes or is provided by an arginine bicarbonate solution. For example, the amino acid may be provided by an about 40% solution of the basic amino acid, such as arginine bicarbonate or alternatively called as arginine carbamate. In some embodiments, the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.

The oral care composition of the invention may comprise a zinc ion source. The zinc ion source may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc picolinate, zinc proprionate, zinc salicylate, zinc silicate, zinc stearate, zinc tartrate, zinc undecylenate, and mixtures thereof. In some embodiments, the zinc ion source is present in an amount of from 0.01% to 5%, e.g., 0.1% to 4%, or 1% to 3%, by weight of the composition.

In some embodiments, the zinc ion source is selected from zinc oxide, zinc citrate, and a combination thereof. Zinc oxide may be present in an amount of 0.5% to 2%, e.g., 0.5% to 1.5%, or about 1% by weight of the composition. Zinc citrate may be present in an amount of 0.1% to 1%, 0.25% to 0.75%, about 0.5% by weight of the composition by weight of the composition. In some embodiments, the composition comprises zinc oxide and zinc citrate. The composition may comprise zinc oxide in an amount of 0.5% to 2%, e.g., 0.5% to 1.5%, about 1% or about 1.2% by weight of the composition and zinc citrate in an amount of 0.1% to 1%, 0.25% to 0.75%, about 0.5% by weight of the composition. In certain embodiments, the composition comprises zinc oxide in an amount of about 1% by weight of the composition and zinc citrate in an amount of about 0.5% by weight of the composition.

The oral care compositions of the present invention may include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically from 0.01% to 5%, from 0.01% to 2%; or from 1% to 2%; or about 1.5%, by weight of the composition. In some embodiments, the composition may comprise sodium lauryl sulfate. In some embodiments, the composition may comprise a betaine zwitterionic surfactant and a non-ionic block copolymer. The betaine zwitterionic surfactant may be a $C_8$-$C_{16}$ aminopropyl betaine, e.g., cocamidopropyl betaine. In some embodiments, the betaine zwitterionic surfactant, e.g., cocamidopropyl betaine, is present in an amount of from 1% to 1.5%, from 1.1% to 1.4%, from 1.2% to 1.3%, or about 1.25% by weight of the composition. The non-ionic block copolymer may be a poly(propylene oxide)/poly(ethylene oxide) copolymer. In some embodiments, the copolymer has a polyoxypropylene molecular mass of from 3000 to 5000 g/mol and a polyoxyethylene content of from 60 to 80 mol %. In some embodiments, the non-ionic block copolymer is a poloxamer. In some embodiments, the non-ionic block copolymer is selected from: Poloxamer 338, Poloxamer 407, Poloxamer, 237, Poloxamer, 217, Poloxamer 124, Poloxamer 184, Poloxamer 185, and a combination of two or more thereof. In some embodiments, the copolymer is Poloxamer 407, which is available in commerce as Pluronic F-127 (Pluronic is a trademark of BASF Corporation). In some embodiments, the non-ionic block copolymer, e.g., poloxamer, e.g., poloxamer 407, is present in an amount of from 0.3% to 0.7%, from 0.4% to 0.6%, or about 0.5% by weight of the composition.

The oral care composition of the invention may include additional thickeners other than the thickening silica having a particle size distribution (D95) less than or equal to 7 μm and a BET surface area of greater than or equal to 150 $m^2/g$. Suitable additional thickeners may be any orally acceptable thickener or thickening agent configured to control the viscosity of the oral care composition. Illustrative thickeners may be or include, but are not limited to, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. The thickening system may also include POLYPLASDONE® XL 10F, which is commercially available from Ashland Inc. of Covington, KY Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, MI), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof. Thickeners particularly suitable of use in the oral care composition of the invention include natural and synthetic gums and colloids. Optionally, the composition comprises at least one gum selected from carrageenan and xanthan gum.

In some embodiments, the oral care compositions may include one or more abrasives or an abrasive system including one or more abrasives. As used herein, the term "abrasive" may also refer to materials commonly referred to as "polishing agents". Any orally acceptable abrasive may be used, but preferably, type, fineness (particle size), and amount of the abrasive may be selected such that the tooth enamel is not excessively abraded in normal use of the oral care composition.

The one or more abrasives may have a particle size or D50 of less than or equal to about 10 μm, less than or equal to about 8 μm, less than or equal to about 5 μm, or less than or equal to about 3 μm. The one or more abrasives may have a particle size or D50 of greater than or equal to about 0.01 μm, greater than or equal to about 0.05 μm, greater than or equal to about 0.1 μm, greater than or equal to about 0.5 μm, or greater than or equal to about 1 μm. Illustrative abrasives may include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate (e.g., precipitated calcium carbonate and/or natural calcium carbonate), magnesium carbonate, hydrated alumina, silica, zirconium silicate, aluminum silicate including calcined aluminum silicate, polymethyl methacrylate, or the like, or mixtures and combinations thereof. In some embodiments, the oral care composition comprises an abrasive silica.

In some embodiments, the oral care composition of the invention comprises a calcium-containing abrasive (e.g., calcium carbonate). In some embodiments, the calcium-containing abrasive is selected from calcium carbonate, calcium phosphate (e.g., dicalcium phosphate dihydrate), calcium sulfate, and combinations thereof. In a preferred embodiment, the oral care composition comprises calcium carbonate as an abrasive. In one embodiment, the oral care composition comprises precipitated calcium carbonate or natural calcium carbonate. Precipitated calcium carbonate may be preferred over natural calcium carbonate.

The amount or concentration of the one or more abrasives present in the oral care composition may vary widely. In some embodiments, the amount of the abrasives present in the oral care composition may be from about 15 weight % to about 70 weight %, e.g., from about 20 weight % to about 50 weight %, from about 25 weight % to about 45 weight %, from about 30 weight % to about 40 weight %, from about 10% to about 20 weight %, or about 15 weight %, based on a total weight of the oral care composition.

In some embodiments, the oral care compositions of the invention may include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In some embodiments, the composition comprises a humectant selected from glycerin, sorbitol and a mixture thereof. In some embodiments, the humectant may be present in an amount of from 20% to 60%, for example from 15% to 40%, from 15% to 35%, from 20% to 40%, from 30% to 50%, from 30% to 40%, or from 40% to 45%, by weight of the composition. In some embodiments, the composition comprises glycerin or sorbitol, optionally wherein glycerin or sorbitol is present in an amount of from 15% to 40%, from 20% to 40%, from 30% to 40%, or about 35% by weight of the composition.

The oral care compositions of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care compositions of the present invention may include a sweetener such as, for example, saccharin, for example sodium saccharin, acesulfame, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The oral care compositions of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The oral care composition of the invention may include anticalculus agents. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent includes tetrasodium pyrophosphate (TSPP), sodium tripolyphosphate (STPP), or a combination thereof.

The oral care composition of the invention may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition of the invention may include one or more pigments, such as whitening pigments. In some embodiments, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

All ingredients for use in the compositions described herein should be orally acceptable. As used herein, "orally acceptable" may refer any ingredient that is present in a composition as described in an amount and form which does not render the composition unsafe for use in the oral cavity.

In another aspect, the invention provides a method to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, comprising applying an effective amount of any of oral care compositions as disclosed herein to the oral cavity of a subject in need thereof. The method may include contacting the oral care composition with water. The method may also include contacting the surface of the teeth with the oral care composition. Contacting the surface of the teeth with the oral care composition may include disposing the oral care composition (e.g., toothpaste) on a toothbrush and brushing the teeth with the toothbrush. The oral care composition may be applied and/or contacted with the surfaces of the teeth at predetermined intervals. For example, a daily basis, at least once a day, twice a day, or more, for multiple days, or alternatively every other day. In another example, the oral care composition may be applied and/or contacted with the surfaces of the teeth at least once a day, at least once every two days, at least once every three days, at least once every five days, at least once a week, at least once every two weeks, or at least once a month. The oral care composition thereof may be utilized for up to 2 weeks, up to 3 weeks, up to 4 weeks, up to 6 weeks, up to 8 weeks, or greater.

In another aspect, the invention provides the use of any of oral care compositions as disclosed herein to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, in a subject in need thereof.

In another aspect, the invention provides a method of preparing a thickening silica loaded with fluoride, which comprises mixing a thickening silica and a fluoride ion source in an aqueous solution (e.g., water) at a pH below 5.5, e.g., from 3.5 to 5.5, from 3.5 to 5.0, from 3.5 to 4.5, from 4.0 to 5.0, from 4.0 to 4.5, from 3.5 to 4.0, from 3.8 to 4.2, or about from 4.0, wherein the thickening silica has a particle size distribution (D95) less than or equal to 7 µm and a BET surface area of greater than or equal to 150 m²/g. In some embodiments, the thickening silica may have a BET surface area of greater than or equal to 175 m²/g, greater than or equal to 200 m²/g, or greater than or equal to 250 m²/g. In some embodiments, the thickening silica may have an oil absorption of greater than or equal to about 200 mL/100 g, about 240 mL/100 g, or about 250 mL/100 g. In some embodiments, the thickening silica may have an average particle size of from about 3 µm to about 5 µm, from about 3 µm to about 4 µm, or about 3.5 µm. In a preferred embodiment, the thickening silica is Tixosil 331. A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In a preferred embodiment, the fluoride ion source includes sodium fluoride.

In another aspect, the invention provides an oral care composition comprising a thickening silica loaded with fluoride prepared by any of methods as disclosed herein. The fluoride absorbed on the thickening silica is released at pH of 8.0.

EXAMPLES

Thickening silica loaded with fluoride (also referred to as silica fluoride) was prepared as follows. 10,000 ppm fluoride solution was prepared by dissolving 2.2 g sodium fluoride in water, followed by pH adjustment with HCl to pH=4.0. 5 g thickening silica (Tixosil 331 from Solvay) was suspended in the fluoride solution. Under this condition, 0.93 g out of the 1.00 g fluoride initially dissolved in the solution were bound to the silica, to give a fluoride load on the silica corresponding to 18.6%.

The release of fluoride from the silica fluoride was measured by changing the pH of the silica fluoride solution up to 8.5. The result is shown in FIG. 1. Above pH 7.5, fluoride was fully released from the silica fluoride, indicating that the absorption process can be easily reversed by changing the pH to about 8. This is a very interesting working range, as it allows to formulate oral care preparations having a low pH, around 4.5, with most of fluoride absorbed on the silica. During use, fluoride will be released in the mouth after equilibration at the physiological pH in the oral cavity, which is approximately 7 to 8.

Figure 2:
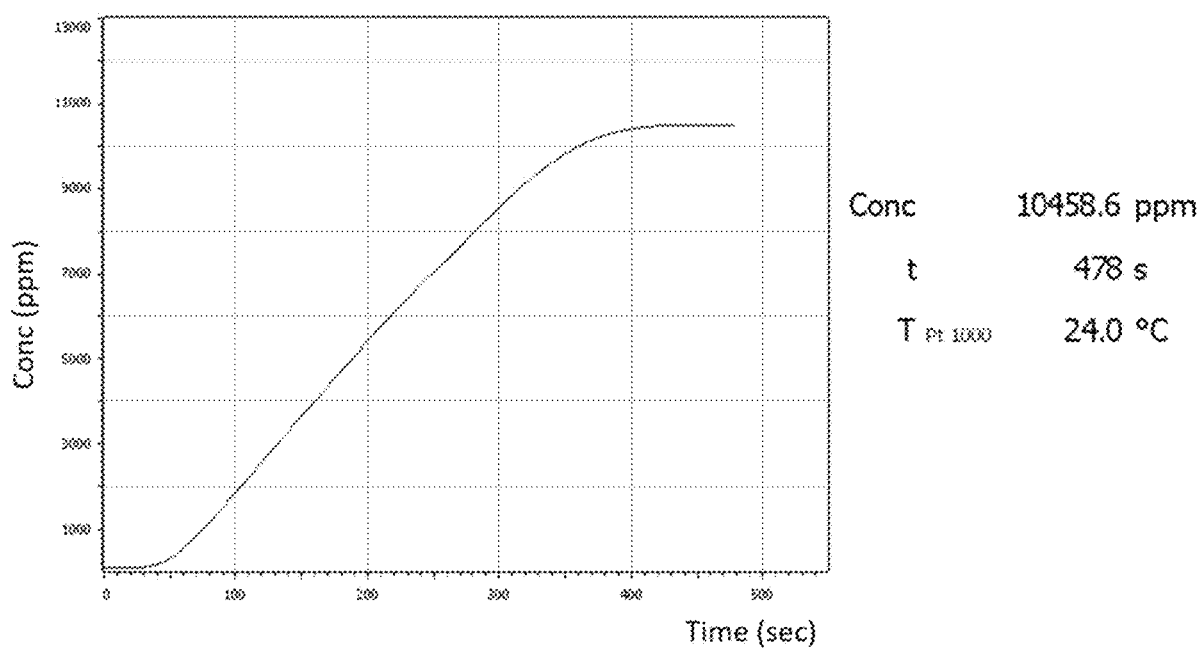
FIG. 2 is a graph showing the release of fluoride from the silica fluoride over time after pH of the solution is changed from 4 to 8 in one step.

Next, the dynamics of the release of fluoride from the silica fluoride after pH is changed was determined at room temperature (24.0° C.). In this Experiment, released fluoride was measured over time up to 478 seconds after pH was changed from 4 to 8 in one step. The result is shown in FIG. 2. Fluoride was released from the silica slowly and the plateau was reached in approximately 400 seconds, which is 3-4 times more than a normal teeth brushing time. This result shows that the release is slow enough to possibly allow the silica to reach and adhere on the dentin.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

The invention claimed is:

1. An oral care composition comprising an orally acceptable vehicle, a thickening silica and a fluoride ion source, wherein fluoride is absorbed on the thickening silica, wherein the thickening silica has a particle size distribution (D95) less than or equal to 7 μm and a BET surface area of greater than or equal to 150 m$^2$/g, and wherein the pH of the composition is below 5.5;
wherein the thickening silica loaded with fluoride is made by mixing the thickening silica and the fluoride ion source in an aqueous solution at a pH below 5.5;
wherein the fluoride ion source is selected from sodium fluoride, stannous fluoride, potassium fluoride, sodium monofluorophosphate, amine fluoride, ammonium fluoride, and a combination thereof; and
wherein the release of fluoride plateaus at approximately 400 seconds when measured at 24° C.

2. The composition of claim 1, wherein the thickening silica has a BET surface area of greater than or equal to 175 m$^2$/g, greater than or equal to 200 m$^2$/g, or greater than or equal to 250 m$^2$/g.

3. The composition of claim 1, wherein the thickening silica has an average particle size of from 3 μm to 5 μm.

4. The composition of claim 1, wherein the thickening silica has an oil absorption of greater than or equal to 200 mL/100 g.

5. The composition of claim 1, wherein the thickening silica is present in an amount of from 1% to 20% by weight of the composition.

6. The composition of claim 1, wherein the fluoride ion source is sodium fluoride.

7. The composition of claim 1, wherein the fluoride ion source is present in an amount sufficient to supply 25 ppm to 5,000 ppm of fluoride ions.

8. The composition of claim 1, wherein the amount of fluoride absorbed on the thickening silica is from 1% to 20% by weight of the thickening silica.

9. The composition of claim 1, wherein the pH of the composition is from 3.5 to 5.5.

10. The composition of claim 1, wherein the fluoride absorbed on the thickening silica is released at pH of 8.0.

11. The composition of claim 1, wherein the composition is selected from the group consisting of toothpaste, gel, water free toothpaste, toothpowder, and dental varnish.

12. A method of (i) reducing or inhibiting formation of dental caries, (ii) reducing, repairing or inhibiting precarious lesions of the enamel, (iii) reducing or inhibiting demineralization and promoting remineralization of the teeth, (iv) reducing hypersensitivity of the teeth, (v) reducing or inhibiting gingivitis, (vi) promoting healing of sores or cuts in the oral cavity, (vii) reducing levels of acid producing bacteria, (viii) reducing or inhibiting microbial biofilm formation in the oral cavity, (ix) reducing or inhibiting plaque formation in the oral cavity, (x) promoting systemic health, or (xi) cleaning teeth and oral cavity, comprising applying an oral care composition according to claim 1, to the oral cavity.

13. The composition of claim 3 wherein the thickening silica has an average particle size of from 3 μm to 4 μm.

14. The composition of claim 13 wherein the thickening silica has an average particle size of about 3.5 μm.

15. The composition of claim 4, wherein the thickening silica has an oil absorption of greater than or equal to 240 mL/100 g.

16. The composition of claim 15, wherein the thickening silica has an oil absorption of greater than or equal to 250 mL/100 g.

* * * * *